(12) United States Patent
Levine

(10) Patent No.: US 8,419,306 B1
(45) Date of Patent: Apr. 16, 2013

(54) SINGLE USE TOOTHBRUSH AND WHITENING TOUCH UP DEVICE AND DERMATOLOGICAL APPLICATOR

(76) Inventor: Jonathan B. Levine, Purchase, NY (US)

( * ) Notice: Subject to any disclaimer, the term of this patent is extended or adjusted under 35 U.S.C. 154(b) by 26 days.

(21) Appl. No.: 12/567,120

(22) Filed: Sep. 25, 2009

(51) Int. Cl.
*B43M 11/06* (2006.01)

(52) U.S. Cl.
USPC .............................. 401/183; 401/184; 401/266

(58) Field of Classification Search .......... 401/183–187, 401/265, 266
See application file for complete search history.

(56) References Cited

U.S. PATENT DOCUMENTS

| 3,937,235 | A | * | 2/1976 | Broughton | .................... 401/186 |
|---|---|---|---|---|---|
| 6,254,297 | B1 | | 7/2001 | Frazier | |
| D504,775 | S | | 5/2005 | Frazier | |
| 6,902,397 | B2 | | 6/2005 | Farrell et al. | |
| 6,929,475 | B1 | | 8/2005 | Dragan | |
| 7,044,671 | B2 | * | 5/2006 | Parikh et al. | .................. 401/183 |
| 7,201,577 | B2 | | 4/2007 | Levine | |
| 7,597,497 | B2 | | 10/2009 | Levine | |
| 7,891,899 | B2 | * | 2/2011 | Tani | .............................. 401/266 |
| 2007/0020028 | A1 | | 1/2007 | Levine | |
| 2007/0166666 | A1 | | 7/2007 | Levine | |

* cited by examiner

*Primary Examiner* — Tuan N Nguyen
(74) *Attorney, Agent, or Firm* — H. Jay Spiegel

(57) ABSTRACT

An applicator having a squeezable vessel, an applicator tip, a crenellated ring and a sponge. The vessel contains contents that react upon contact with a reactive ingredient treated onto the sponge. By squeezing the vessel, the contents are urged to leave the vessel to pass through a hollow of the applicator tip to reach the sponge. The sponge has a peripheral edge that faces inward facing surfaces of elastomeric formations of the crenellated ring. The elastomeric formations are each separated from each other in succession. The elastomeric formations at the distal end of the crenellated ring may have a greater depth than that of the sponge, which in turn may have a greater depth than elastomeric formation(s) at a proximal end of the crenellated ring.

8 Claims, 3 Drawing Sheets ically transported, single use toothbrush and whitening touch up device and dermatological applicator

SINGLE USE TOOTHBRUSH AND WHITENING TOUCH UP DEVICE AND DERMATOLOGICAL APPLICATOR

FIELD OF THE INVENTION

The present invention relates to an applicator in the form of an easily transported, single use toothbrush and whitening touch up device. The present invention also relates to a single use dermatological applicator that enables administration of a dermatological compound to skin, for example, to treat an existing condition of the skin or prevent a skin condition from arising.

BACKGROUND OF THE INVENTION

There is a need for a single use toothbrush and whitening touch up device that is easily transported. Such a device should allow to reactive ingredients to contact each other to react with each other both when and where they are to be applied to tooth surfaces.

SUMMARY OF THE INVENTION

One aspect of the present invention relates to an applicator having a squeezable vessel, an applicator tip, a crenellated ring and a sponge. The vessel contains contents that react upon contact with a reactive ingredient treated onto the sponge. By squeezing the vessel, the contents are urged to leave the vessel to pass through a hollow of the applicator tip to reach the sponge. The sponge preferably has a peripheral edge that faces inward facing surfaces of elastomeric formations of the crenellated ring. The elastomeric formations are each separated from each other in succession to provide respective gaps therebetween. The elastomeric formations at the distal end of the crenellated ring may have a greater height than that of the sponge, which in turn may have a greater height than elastomeric formation(s) at a proximal end of the crenellated ring.

BRIEF DESCRIPTION OF THE DRAWINGS

For a better understanding of the present invention, reference is made to the following description and accompanying drawings, while the scope of the invention is set forth in the appended claims.

DETAILED DESCRIPTION OF THE INVENTION

Figure 1:
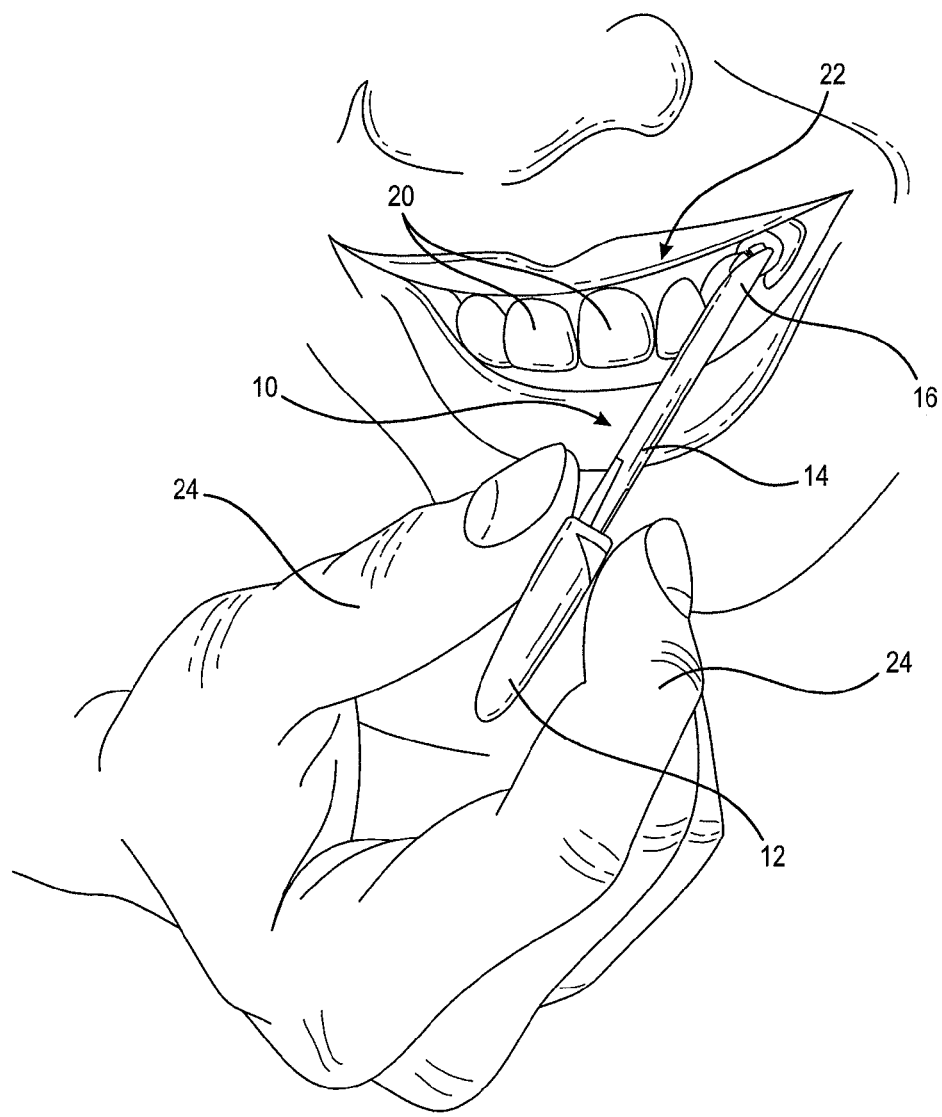
FIG. 1 is an isometric view of the single use toothbrush and whitening touch up device of the present invention whose dispenser tip is being applied on a tooth surface.
Figure 2A:
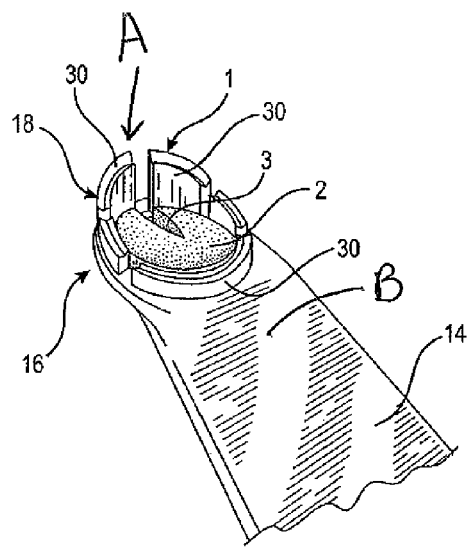
FIG. 2A is an isometric view of a crenellated ring and sponge at the dispenser tip of FIG. 1.
Figure 2B:
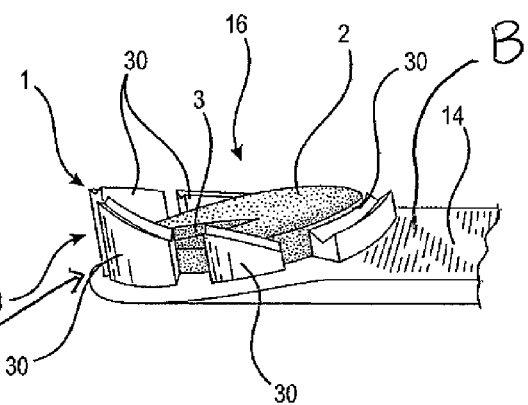
FIG. 2B is a left side plan view of the crenellated ring and the sponge of FIG. 1, which view is symmetric to the right side.
Figure 2C:
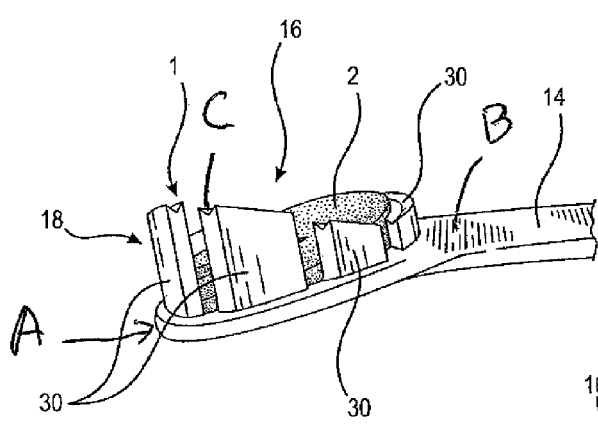
FIG. 2C is an isometric view of the left side as in FIG. 2B but rotated slightly more to the right.
Figure 2D:
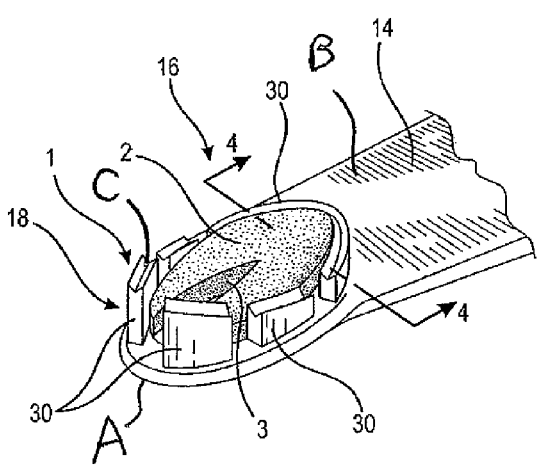
FIG. 2D is an isometric view of the left side as in FIG. 2C but rotated further to the right and to the top.

Referring to FIG. 1, an easily transported, single use toothbrush and whitening touch up device 10 is shown in use to brush and whiten tooth surfaces 20 in a mouth 22. The device 10 is held between fingers 24, and when squeezed, causes contents from a vessel or sealed reservoir portion 12 to be urged out of the vessel 12 and expelled through an extended application tip 14. Preferably, the user squeezes the device 10 to cause all of the contents of the vessel 12 to be completely expelled through the application tip 14. To enable the contents of the vessel to be urged out therefrom, the vessel 12 is preferably provided with a collapsible wall. However, instead of the collapsible wall, other arrangements or mechanism that enable manual pressure applied to the device 10 to cause discharge of the contents of the vessel 12 therefrom may also be used in accordance with the invention.

FIG. 1 illustrates how the extended application tip 14 allows the user to reach tooth surfaces 20, including rear molars, without the need to put fingers in the mouth 22. The extended application tip 14 terminates at a distal end forming a dispensing tip 16. The dispensing tip 16 is over-molded with elastomeric formations 30 extending outwardly from a side of an end of the applicator tip (FIGS. 2A-2D, 3A-3C, 4) to provide a compliant application surface, which conforms to the surfaces 20 of the teeth.

Referring to FIGS. 2A-2D, the elastomeric formations 30 are shaped to form a crenellated ring 1. As shown, the crenellated ring 1 is discontinuous in that the elastomeric formations 30 are separated from one another by gaps, i.e., a gap between each respective pair of adjacent elastomeric formations 30, but the invention is not limited to a discontinuous, crenellated ring. The elastomeric formations 30 each have an inward facing surface that faces, and may even abut, an outwardly facing peripheral edge of a sponge 2.

The height of the sponge 2 is preferably smaller in dimension than a height of the elastomeric formations 30 at the distal end 18 of the crenellated ring 1, but greater in dimension than a height of the elastomeric formation(s) 30 at the proximal end of the crenellated ring 1.

The sponge 2 is treated preferably with bicarbonate of soda, which reacts to enhance the efficacy of the gel being dispensed through fluid passage 3. The sponge 2 also retains the gel during the application and brushing process and provides further scrubbing function on the tooth surfaces 20.

The crenellated ring 1 is formed so that a portion, preferably the distal end 18, is raised and can be used to reach into the crevasses between teeth. The crenellated ring 1 may be considered to exhibit a series of indents or notches that are spaced apart from each other. Thus, the crenellated ring 1 may be provided by any structure that has a plurality of indents or notches, with material therebetween to form projections (such as the elastomeric formations 30).

Figure 3A:
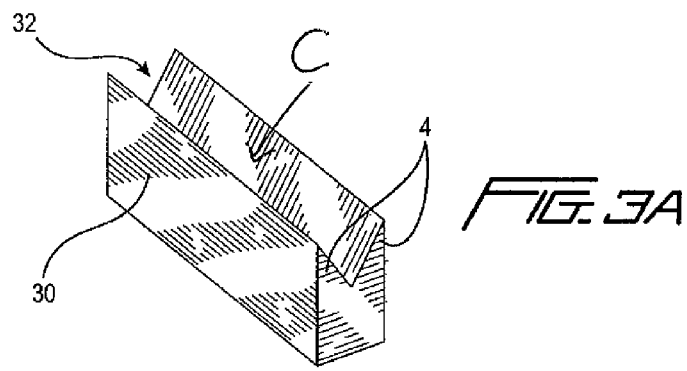
FIG. 3A is an isometric view of a recessed V-shape embodiment of a top surface of the crenellated ring of FIGS. 2A-2D.
Figure 3B:
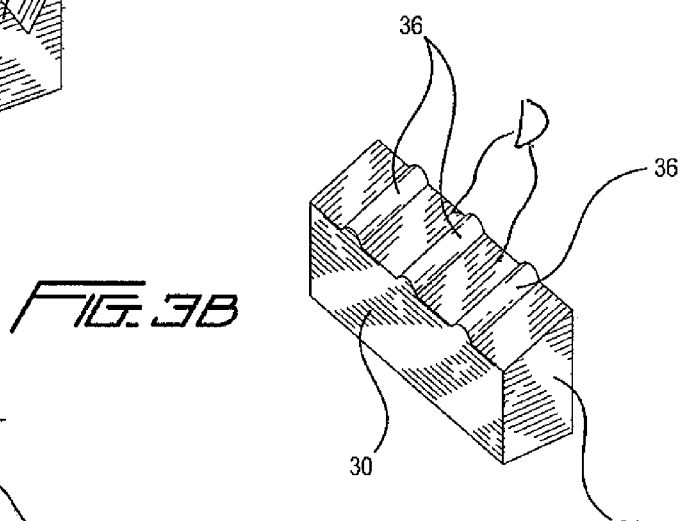
FIG. 3B is an isometric view of a projecting V-shape embodiment of the top surface of the crenellated ring of FIGS. 2A-2D.
Figure 3C:
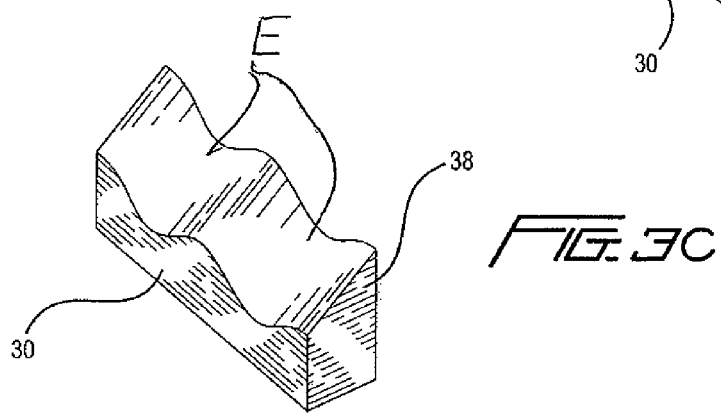
FIG. 3C is an isometric view of a sinusoidal, wavy embodiment of the top surface of the crenellated ring of FIGS. 2A-2D.

A top surface of the ring 1 may be contoured with recessed areas into any one of a variety of different shapes, such as those of FIGS. 3A-3C, to enhance conformity and reach of the whitening touch up device and brush. In the case of FIG. 3A, the elastomeric formation 30 takes on a recessed V-shape 32. In the case of FIG. 3B, the elastomeric formation 30 takes on a projecting V-shape 34 with spaced apart projections 36. In the case of FIG. 3C, the elastomeric formation 30 takes on a sinusoidal, wavy shape 38.

Figure 4:
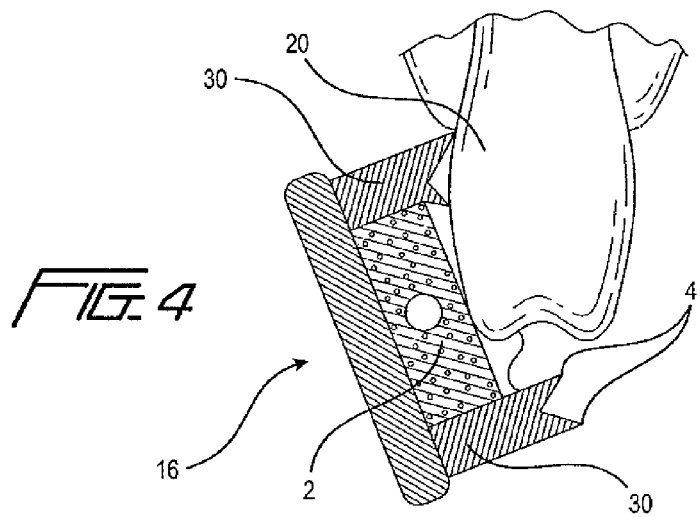
FIG. 4 is an end view of crenellated ring and the sponge of FIG. 1 being applied to a tooth surface.

Indeed, the top surface of the ring may have sharp edges 4, which, as seen in FIG. 4, serve to squeegee the teeth and massage the gum line.

The applicator of the present invention may be used for any combination of ingredients that react upon contact. One of the ingredients is within the vessel or sealed reservoir portion 12 while the other reactive ingredient is within or impregnated into the sponge 2.

The device 10 is not limited to use for whitening and brushing teeth but may also be used for dermatological and skin care applications, e.g., to apply a skin care product to skin to treat an existing condition of the skin or prevent a skin condition from arising. In such cases, the vessel 12 would be provided with one compound while the sponge 2 would be provided with another compound that reacts with the compound in the vessel 12 to provide the desired dermatological or skin care effect. In this embodiment, or in other embodiments, the sponge 2 may be replaced with another type of applicator that is better suited for the particular dermatological of skin care compound. In addition, the elastomeric formations 30 may be provided with the variable depth described above and shown in FIGS. 2A-2D or provided with the same depth, and also provided with any of the contours shown in FIGS. 3A-3C or a flat upper surface.

Even more generally, the device 10 may be used for other applications wherein a compound is to be applied to a surface and the compound may be constituted by two different ingredients that react upon contact to form the compound.

While the foregoing description and drawings represent the preferred embodiments of the present invention, it will be understood that various changes and modifications may be made without departing from the scope of the present invention.

What is claimed is:

1. An applicator, comprising a vessel, an elongated applicator tip, a sponge and a crenellated ring surrounding the sponge, each extending outwardly from a side of an end of said applicator tip, the crenellated ring having a plurality of elastomeric formations, each spaced from each other in succession by respective gaps, each elastomeric formation having a distal surface with at least one recessed area, the vessel containing contents and a mechanism that enables the contents to be urged out of the vessel through an opening in the vessel under manual pressure, the applicator tip being in fluid communication with the opening to receive the contents urged out from the vessel, the applicator tip being hollow to allow the contents to pass through the applicator tip to dispense through a distal opening of the applicator tip to reach the sponge, the distal opening being spaced away from the vessel, the sponge being treated with a reactive ingredient that reacts upon contact with the dispensed contents that reach the sponge.

2. The applicator of claim 1, wherein the elastomeric formations each have an outward surface configuration including said at least one recessed area, the outward surface configuration being selected from a group consisting of a recessed V-shape, a projecting V-shape, and a sinusoidal, wavy shape.

3. The applicator of claim 1, wherein the sponge has a peripheral edge facing outward toward inward facing surfaces of the elastomeric formations of the crenellated ring.

4. The applicator of claim 3, wherein the inward facing surfaces of the elastomeric formations abut the outward facing peripheral edge of the sponge.

5. The applicator of claim 1, wherein the crenellated ring has a distal end portion and a proximal end portion, the distal end portion being further away from the vessel than the proximal end portion, the elastomeric formations at the distal end portion having a height that is greater in dimension than that of proximally located elastomeric formations.

6. The applicator of claim 5, wherein the height of the elastomeric formations at the distal end portion is greater in dimension than a height of the sponge.

7. The applicator of claim 5, wherein a height of the elastomeric formations at the proximal end portion is smaller in dimension than the height of the sponge.

8. The applicator of claim 1, wherein the contents of the vessel include a gel and the reactive ingredient of the sponge is bicarbonate soda.

\* \* \* \* \*